United States Patent [19]
Legarda Ibanez

[11] Patent Number: 6,103,734
[45] Date of Patent: *Aug. 15, 2000

[54] DRUG COMBINATION AS A MEDICAMENT TO SUPPRESS THE DEPENDENCE OF INDIVIDUALS TO OPIATES

[76] Inventor: Juan Jose Legarda Ibanez, Avenida Eduardo Dato 34, 5-A, E-41005 Sevillia, Spain

[*] Notice: This patent issued on a continued prosecution application filed under 37 CFR 1.53(d), and is subject to the twenty year patent term provisions of 35 U.S.C. 154(a)(2).

[21] Appl. No.: 08/666,533

[22] PCT Filed: Nov. 4, 1994

[86] PCT No.: PCT/ES94/00108

§ 371 Date: Aug. 27, 1996

§ 102(e) Date: Aug. 27, 1996

[87] PCT Pub. No.: WO96/14071

PCT Pub. Date: May 17, 1996

[51] Int. Cl.[7] .................. A61K 31/44; A61K 31/415; A61K 31/34; A61K 31/55
[52] U.S. Cl. .................. 514/282; 514/392; 514/471; 514/220; 514/617; 514/338
[58] Field of Search ................ 514/392, 471, 514/220, 282, 617, 338

[56] References Cited

PUBLICATIONS

Drug and Alcohol Dependence, vol. 35, No. 2, pp. 91–93, J.J. Legarda 'A 24–h inpatient detoxification treatment for heroin addicts: a preliminary investigation' cited in the application, 1994.
Am J Psichiatry, vol. 150, No. 5, p. 839, N. Loimer 'ultrashort nonivasive opiate detoxification', 1993.
Br. J. Addict. vol. 83, No. 5, pp. 567–575 E. Vining 'Clinical utility of rapid clonidine–naltrexone detoxification for opioid abusers',1988.
Br. J. Psichiatry vol. 153, pp. 340–343 C. Brewer 'Opioid withdrawal and naltrexone induction in 48–72 hours with minimal drop–out, using a modification of the naltrexone–clondine technique',1988.
J. Florez Farmecologia Humana Ediciones Cientificas Y Tecnicas, S.A. Barcelona, 1992.
"Dropping out of substance abuse treatment: a clinically oriented Review", Clin. Psychol. Rev., 12, pp. 93 to 116; p. 115, 1993.
"Dropping out of substance abuse treatment: a clinically oriented Review", Clin. Psychol. Rev., 12, pp. 93 to 116; p. 109, 1993.
"Rapid detoxification from opioid dependence", Am. J. Psychiatry 146, 1989.
"Rapid opiate detoxification with Clonidine and Nalozone", Riordan et al., Lancet I, 1980.
"Substance Abuse Disorders: A Psychiatric Priority", Am J. Psychiatry 148, pp. 1291–1300, 1991.
"Technique for Greatly Shortening the Transition from Methadone to Naltrexone Maintenance of Patients Addicted to Opiates", Loimer et al. In Am. J. Psychiatry. 148. 1991.
"The Drug Dependence Clinical Research and Treatment Unit, The Maudsley and Bethlem Royal Hospitals", Strang, et al., 83 pp. 1387–1394, 1988.
"Treatment of Heroin addicts using Buprenorphine", Am. J. Drug Alcohol Abuse 17, 1991.

*Primary Examiner*—William R. A. Jarvis
*Attorney, Agent, or Firm*—Merchant & Gould P.C.

[57] ABSTRACT

Combination of chemical compounds used as a medicament intended to suppress the dependence of individuals to opioids, the combination comprising a laxative or enema of irrigation, repeated doses of alpha-adrenergic agents, anticmetic agents, gastric protectors, optionally inhibitors of the proton pump, an anxiolytic compound, anaesthetic sleep inducing agent and determined doses of an opioid antagonist compound, such as nazalone or naltrexone.

17 Claims, No Drawings

DRUG COMBINATION AS A MEDICAMENT TO SUPPRESS THE DEPENDENCE OF INDIVIDUALS TO OPIATES

This application is a 371 of PCT/E594/00108, filed Nov. 4, 1994.

The present description relates to an invention based on the combination of certain chemical compounds or drugs thanks to which the detoxification procedure of opiate drug-dependants is carried out in less than a 24 hour period.

One of the main objectives in the treatment of opiate addiction is abstinence, which is dealt with in several papers as the article "Substance abuse disorders: a psychiatric Priority" in Am. J. Psychiatry 148, pp. 1291 to 1300, written by the Group for the Advancement of Psychiatry of the committee on Alcoholism and Addictions, in 1991.

There are several rapid procedures in which detoxification takes more than 10 days to be completed, as it is reported in various papers such as "Dependence clinical research and treatment unit, the Maudsley and Bethlem Royal Hospital" in Br. J. Addict. 83 pp. 1387 to 1394, by J. S. Strang, M. Gossop and B. Bradley in 1988.

A publication on the same lines was written by T. R. Kosten, J. H. Kristal, D. S. Charney, L. H. Price, C. H. Morgan and H. D. Kleber in 1989 with the title "Rapid detoxification from opioid dependence" in American Journal of Psychiatry 146, yet another article was written also by said authors, Kosten et al.: "Treatment of Heroin addicts using Buprenorphine" in Am. J. Drug Alcohol Abuse 17, 1991.

The procedures described in the cited articles are often costly, as well as being frustating because of high rate of abandonment. For inpatient detoxification, the drop-out rate varies between 20 and 30% as reported in the article "Dropping out of substance abuse treatment: a clinically oriented Review" in Clin. Psychol. Rev., 12; pp 93–116, whereas for out-patient detoxification, it may be as high as 80%, as reported in the article by M. Gossop, A. Johns and L. Green "Opiate withdrawal: inpatient versus outpatient programmes and preferred versus random assignment to treatment" in Br. Med. J. 293; 1986.

Detoxification methods may involve replacement of the drug, using an opiate agonist such as Methadone, as reported in the article "Opiate withdrawal responses to 10-day and 21-day Methadone withdrawal programmes" by M. Gossop et al. in British Journal of Psychiatry, 154; 1989, or using partial opiate agonists such as Buprenorphine, as reported in "Human Pharmacology and abuse potential of the analgesic Buprenorphine by Jasinski et al. in Arch. Gen. Psychiatry 35; 1978. Another approach involves the use of adrenergic agonists such as clonidine or Guanphacine as reported in the articles "Clonidine in opiate withdrawal" by M. S. Gold et al. in Lancet i, 1978 and "Preliminary results of the Guanphacine treatment of acute opiate withdrawal" by Schubert et al. in America Journal of Psychiatry, 141.

Recently, there is a rising interest in blockade treatments using opiate antagonists such as Naloxone or Naltrexone in conjuction with adrenergic agonists, as reported in the papers "Rapid opiate detoxification with Clonidine and Naltrexone" by Riordan et al. published in 1980 in Lancet i, and in "The combined use of Clonidine and Naltrexone as a safe, rapid and effective treatment of abrupt withdrawal from Methadone" by Chartney et al. in Am. J. Psychiatry, 1989, by which it is achieved to realize therapeutics treatments derived from the use of said compounds in a short period between 48 hours and 4–5 days as reported in the articles "Opioid withdrawal and Naltrexone induction in 48–72 hours with minimal drop-out using a modification of the naltrexone-Clonidine technique" by Brewer et al. in Br. J. of Psychiatry, 153; 1988 and "Clinical utility of rapid Clonidine-Naltrexone detoxification for opioid abusers" by E. Vining, T. Kosten and H. Kleber in Br. J. Psychiatry, 83; 1988.

In view of the information published up till now, which has been cited hereabove, it is observed that there is a problem in detoxification, especially with Methadone substitution being the longer duration of the abstinence syndrom. The use of antagonists permits important reduction in the duration of the detoxification process.

In this line, an experiment of treatment with seven patients maintained with Methadone included the addition of an opiate antagonist, Naloxone, a sedative Midazolam, in doses much higher than recomended as well as the use of an antagonist of the sedative, Flumazenil, for returning to sedation. During the treatment, pulse rate and blood pressure were monitored according to the instructions given in the article "Technique for greatly shortening the transition from Methadone to Naltrexone maintenance of patients addicted to opiates" by Loimer er al. in Am. J. Psychiatry, 148; 1991. More recently, a new way for treating twenty patients addicted to Heroin has been used. This procedure was of non-invasive type, that is all medication was supplied orally, and started twelve hours after last consumption of Heroin as reported in the article "Ultrashort non invasive opiate detoxification" by Loimer et al. in Am. J. Psychiatry, 150; 1993. Said procedure consisted of using the same sedative as used in previous experience: Midazolam, but at doses even higher than in the previous case. Said procedure also comprised an alpha-adrenergic agonist: Clonidine, which increases sedation and diminishes the symptomatology of the syndrome of opiate abstinence, and an antiemetic: Ondansetron. To accelerate the detoxification, two opiate antagonists, Naloxone and Naltrexone were used at very high doses: 4 and 50 milligrames, respectively, applied in one single dose.

These two last manners for detoxifying represent, according to the experience that has lead to the use of the collection of compounds being object of the invention, a severe risk for patient's life and are impracticable with the doses of antagonists and sedatives which are employed as well as with the kind of sedatives employed, moreover without an adequate monitoring.

As the most recent paper in this field of Therapeutics, the article "A 24-h. inpatient treatment for heroin addicts: a preliminary investigation", is mentioned, published by the applicant of the present application, in "Drug and Alcohol Dependence", 35 (1994). In said article, several approaches and products in line with those cited so far are indicated, but having certain differences with the products and the use of these products, which will be disclosed in the present description. Said differences are based on the use of certain sedatives and antagonists in doses not as high as before, whereby the doses applied to the organism are the recommended doses for using the product which in the case of antagonists, are in range between 6 and 40 milligrammes, preferably between 10 and 30 milligrammes and more preferably between 12.5 and 18.5 milligrames, and when naltrexone is employed, it is possible to employ, as antagonist, Naloxone in a range of 0.4 to 1.5 milligrammes per hour intravenously. Another difference with respect to what was done up till now by various authors like Loiner, etc., is based on monitoring and sedation in a period longer than 2 hours.

The present invention is directed to a drug combination that allows an ultrarapid approach for the detoxification of polydrug users who are addicted to heroin and/or Methadone or other opiates. The use of certain compounds will be carried out in accordance with some approaches that in the first place can begin, in contrast to other approaches, immediately after the patient has done his last opiate intake, because of which there is no need for waiting as in other treatments, and, further, it is not necessary to substitute one opiate by another before beginning the supplying of the products for detoxification of the present invention. A further novelty is the incorporation of one of the anesthetic sleeping agents used, Propophol, a drug which has never been employed by other specialist in this field, and which, as well as any other, e.g. Midazolam, can be supplied according to the recommended therapeutical doses without the necessity of dangerously increasing the dosage.

On the other hand, patient monitoring should essentially include blood pressure measurement, heart rate and Oxygen saturation in arterial blood. This last paramenter has not been employed before by other specialists in this field. Additionally, it is to be said that products of the invention are used through invasive-kind procedures. Similarly, sedation and/or anesthesia are monitored for a period of, at least, three hours. Minimum requirements for carrying out this type of intervention are a secretions aspirator and an apparatus for assisted respiration. Therefore, the drug application has to be done in the proximity of an intensive care unit or in such a center, or in a hospital room in the presence of all required equipment.

In order to understand the combination of the products comprised in the invention and their purpose in reaching detoxification, the procedure in which they are included is described hereinbelow.

Firstly, patients will be optionally requested to take a laxative, one day before admission, to achieve the best possible intenstinal cleaning, the patient not taking any food at least eight hour prior to intervention. Additionally, a full medical and psychological examination will be carried out, ruling out any sort of pathology that counterindicates the treatment and all neccessary analitical examinations such as hemogram, biochemistry, pregnancy-test in the case that the patient is a female at fertile age, will be carried out as any other complementary examination directed in accordance with the semiology found in physical examination, for example thorax radiography, Computerised axial scanning (CAT), electrocardiogram and electroencephalography. Just prior to hospitalization, repeated doses of alpha-adrenergic antagonists such as Guanfacine or Clonidine will be supplied trying to maintain the blood pressure not lower than 90–60 mm of Hg and the heart-frequency not lower than 55 systoles per minute. Once patient exploration has finished, intervention can begin. In this case, a peripheral vein or, in its absence, a central one will be taken, antiemetics such as Ondansetron and gastric protetants such as H2-antihistaminics, as Ranitidine and/or proton-pump inhibitors such as Omeprazol are supplied and patient sedation or anesthesia is then carried out by means of anesthetic agents such as Propophol or Propophol and a benzodiazepine such as Midazolam, maintaining them in a constant perfusion at a dose adjusted to the response of the patient, and not higher than those recommended by the pharmaceutical laboratory. After that, the opiate antagonist, Naloxone and/or naltrexone is supplied. During the sedation or anesthesia period, the supply of the opiate antagonist will be repeated as required and at doses that depend on the quantity of Heroin that the patient used to take. Each dose of Naltrexone will never exceed 40 milligrammes, neither the whole dose will exceed 50 milligrammes.

When the patient no longer shows signs of opiate withdrawal such as piloerection, rhinorrea and motor agitation, generally four hours after sleep-induction, a Naloxone test is carried out by intravenous supply of 0.8 milligammes of said substance. If results are negative, that is when no withdrawal-sign appears, the anesthetic supply is stopped, the patient is waken up, and preferably an analgesic such as Ketorolac, a H2-antihistaminics such as Ranitidine, a benzodiazepine such as Ketazolam, and an adrenergic agonist such as Guanfacine, is supplied. When finishing drug supply, 24 hours after admission, the patient may be discharged, supplying again an opiate antagonist, having a medium lifetime, such as Naltrexone.

Having described the nature of the present invention, as well as one manner or approach to put this into practice, it only remains to be added that the invention may have a series of variations in parts of its contents as long as said alterations do not substantially vary the characteristics that are claimed below.

I claim:

1. A method for suppressing dependence of a patient upon opiates, the method comprising the steps of:

fasting the patient for eight or more hours;

subjecting the patient to medical and psychological examination to determine any contraindications to administration of agents used in the method;

administering to the fasted patient an alpha-adrenergic agent;

administering to the fasted patient an antiemetic, a gastric protectant, a proton pump inhibitor, or a combination thereof;

administering to the fasted patient a sedating or anesthetizing agent;

administering to the fasted patient an opiate antagonist;

after administration of the opiate antagonist, monitoring the patient for signs of opiate withdrawal;

after monitoring shows insignificant signs of opiate withdrawal, carrying out a Naloxone test;

after a negative result in the Naloxone test, stopping administration of the sedating or anesthetizing agent;

waking the patient; and administering an opiate antagonist to the wakened patient.

2. The method of claim 1, further comprising the step of:

administering a laxative, an enema, or a combination thereof prior to fasting the patient.

3. The method of claim 1, further comprising the step of:

administering to the wakened patient an analgesic, an H2-antihistaminic, a benzodiazepine, an adrenergic agonist, or a combination thereof.

4. The method of claim 3, wherein the benzodiazepine is Midazolam.

5. The method of claim 1, wherein administering to the patient an alpha-adrenergic agent comprises repeated doses of alpha-adrenergic agent.

6. The method of claim 1, wherein the alpha-adrenergic agent is Guanfacine or Clonidine.

7. The method of claim 1, wherein the antiemetic is Ondansetron.

8. The method of claim 1, wherein the gastric protectant is an H2-antihistaminic.

9. The method of claim 8, wherein the gastric protectant is Ranitidine.

10. The method of claim 1, wherein the proton-pump inhibitor is Omeprazol.

11. The method of claim 1, wherein the anesthetic is Propophol, or Propophol in combination with a benzodiazepine.

12. The method of claim 11, wherein the benzodiazepine is Midazolam.

13. The method of claim 1, wherein the opiate antagonist is Naloxone.

14. The method of claim 13, wherein the Naloxone is administered at between 0.4 and 1.5 milligrams per hour.

15. The method of claim 1, wherein the opiate antagonist is Naltrexone.

16. The method of claim 15, wherein the Naltrexone is administered at between 6 and 40 milligrams per hour.

17. The method of claim 16, wherein the Naltrexone is administered at between 12.5 and 18.5 milligrams per hour.

* * * * *